(12) United States Patent
Jung et al.

(10) Patent No.: US 8,906,836 B2
(45) Date of Patent: Dec. 9, 2014

(54) LUBRICATING OIL COMPOSITION

(75) Inventors: Ha Yong Jung, Gyunggi-do (KR);
Myung Hwa Choi, Gyunggi-do (KR);
Wang Hyun Kwon, Gyunggi-do (KR);
Hyung Kyu Kim, Daejeon (KR); Kun Kim, Gyunggi-do (KR)

(73) Assignee: Samsung Electro-Machanics Co., Ltd., Gyunggi-Do (KR)

( * ) Notice: Subject to any disclaimer, the term of this patent is extended or adjusted under 35 U.S.C. 154(b) by 259 days.

(21) Appl. No.: 13/271,368

(22) Filed: Oct. 12, 2011

(65) Prior Publication Data

US 2012/0283161 A1 Nov. 8, 2012

(30) Foreign Application Priority Data

May 6, 2011 (KR) .................. 10-2011-0043052

(51) Int. Cl.
*C10M 105/36* (2006.01)
*C07C 69/44* (2006.01)
*C10M 105/38* (2006.01)

(52) U.S. Cl.
CPC ........ *C07C 69/44* (2013.01); *C10M 2207/2825* (2013.01); *C10N 2220/022* (2013.01); *C10N 2240/204* (2013.01); *C10M 2207/2835* (2013.01); *C10N 2230/74* (2013.01); *C10M 105/36* (2013.01); *C10N 2240/02* (2013.01); *C10N 2220/13* (2013.01); *C10M 105/38* (2013.01)
USPC ............................ 508/465; 508/496; 508/499

(58) Field of Classification Search
USPC ........................................ 508/485, 496–499
See application file for complete search history.

(56) References Cited

U.S. PATENT DOCUMENTS

| | | | | |
|---|---|---|---|---|
| 4,891,161 A * | 1/1990 | Tanikawa et al. | ............. | 508/501 |
| 6,903,056 B2 * | 6/2005 | Nagano et al. | ................ | 508/496 |
| 7,517,838 B2 * | 4/2009 | Kawahara et al. | ............ | 508/485 |
| 7,776,802 B2 * | 8/2010 | Hirata et al. | ................... | 508/485 |
| 7,947,635 B2 * | 5/2011 | Hirata et al. | ................... | 508/485 |
| 8,324,423 B2 * | 12/2012 | Miller et al. | ................... | 560/204 |
| 2005/0130850 A1 * | 6/2005 | Fukuda et al. | ................ | 508/110 |
| 2011/0109995 A1 * | 5/2011 | Kodama et al. | ............ | 360/234.1 |
| 2013/0096042 A1 * | 4/2013 | Oda | .............................. | 508/496 |

FOREIGN PATENT DOCUMENTS

JP 4466850 5/2010

OTHER PUBLICATIONS

Applicant-provided Office Action issued for related Korean Patent Application No. 10-2011-0043052, dated Sep. 28, 2012, and its English summary, also provided by the Applicant.

\* cited by examiner

*Primary Examiner* — Ellen McAvoy

(74) *Attorney, Agent, or Firm* — Ladas & Parry, LLP

(57) ABSTRACT

Disclosed is a lubricating oil composition which includes a diester-based base oil having an asymmetric structure in which the number of carbons of the alkyl chain bound to one ester group with respect to a central atom is two more than that of the alkyl group bound to the other ester group, and which has low viscosity and a comparatively small amount of evaporation at high temperature. When this composition is used for a motor of a small hard disk, power consumption can be reduced and stability at high temperature can be enhanced.

4 Claims, No Drawings

LUBRICATING OIL COMPOSITION

CROSS REFERENCE TO RELATED APPLICATION

This application claims the benefit of Korean Patent Application No. 10-2011-0043052, filed May 6, 2011, entitled "Lubricating oil composition," which is hereby incorporated by reference in its entirety into this application.

BACKGROUND OF THE INVENTION

1. Technical Field

The present invention relates to a lubricating oil composition.

2. Description of the Related Art

A lubricating oil is used to reduce the frictional force that occurs on the frictional surface of machines or to disperse frictional heat generated on the frictional surface, and is utilized in various areas including precision machines, spindles, dynamo, steam turbines, compressors, motors, aircrafts, cylinders, etc.

Generally, a lubricating oil results from mixing 80~90% of a base oil comprising mineral oils (paraffinic, naphthenic, aromatic oil) produced from a process of refining petroleum products or synthetic oils (alkylbenzene, PAO, PAGs, PB, ester, VHVI) with 10~20% of an additive for improving lubrication functionality. Although the properties of a lubricating oil slightly vary depending on its end use, it typically has ① a viscosity maintained to be suitable for the use temperature and simultaneously which should not drastically change even upon changing the use temperature, ② a stable oil film that is formed even under boundary lubrication conditions, and ③ a high stability to heat and oxidation.

The lubricating oil is also utilized for the dynamic fluid bearing of a spindle motor for a hard disk. In the case of a hard disk, products having the large capacity of 1 TB or more are currently available, and hard disks are expected to be developed to have a capacity increased by 1.8 times after one year, 3.2 times after two years, and 10 times after five years. According to the trend to increase hard disk capacity and decrease their sizes, the spindle motor is required to have high-precision rotation and great impact resistance, and thus the lubricating oil of the dynamic fluid bearing is regarded as important because it affects these operations so that the motor satisfies the above requirements.

In particular, in the case of a motor for use in a hard disk having a size of 2.5 inches or less, the lubricating oil is required to have low viscosity so that low power is consumed, and also must be stable at high temperature.

SUMMARY OF THE INVENTION

Accordingly, the present invention has been made keeping in mind the problems encountered in the related art and the present invention is intended to provide a lubricating oil composition, which is stable at high temperature and has low viscosity.

An aspect of the present invention provides a lubricating oil composition, comprising a diester-based base oil represented by Chemical Formula 1 or 2 below.

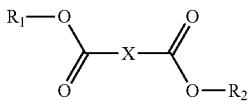

[Chemical Formula 1]

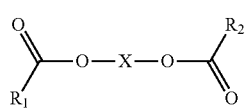

[Chemical Formula 2]

(wherein $R_1$ is a C3~C10 alkyl group,
$R_2$ is different from $R_1$, and is an alkyl group the number of carbons of which is two more than that of $R_1$, and
X is a linear or non-linear C3~C10 alkyl group).

In this aspect, the composition may further comprise one or more additives selected from the group consisting of a cleaning agent, an antioxidant, a viscosity index improver, an anti-wear agent, an anti-corrosive agent, and an antifoaming agent.

In this aspect, the diester-based base oil may be heptyl-nonyl adipate.

In this aspect, the composition may have a viscosity of 13 cP (centipoise) or less at 20° C.

In this aspect, the composition may be used for the fluid bearing of a motor for a hard disk.

DESCRIPTION OF SPECIFIC EMBODIMENTS

The features and advantages of the present invention will be more clearly understood from the following detailed description and embodiments. Furthermore, descriptions of known techniques, even if they are pertinent to the present invention, are considered unnecessary and may be omitted in so far as they would make the characteristics of the invention unclear.

Furthermore, the terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept implied by the term to best describe the method he or she knows for carrying out the invention.

Hereinafter, embodiments of the present invention will be described in detail

According to the present invention, a lubricating oil composition includes a diester-based base oil having an asymmetric structure in which the number of carbons of the alkyl chain bound to one ester group with respect to the central atom is two more than that of the alkyl group bound to the other ester group. The lubricating oil composition according to the present invention has lower viscosity and evaporates less compared to conventional lubricating oil compositions. Thus, in the case where the lubricating oil composition according to the present invention is used for a motor, power consumption of the motor may be reduced, and stability at high temperature may be improved. Below, the lubricating oil composition according to the present invention is more specifically described.

The lubricating oil composition according to the present invention includes, as a base oil, a diester-based compound represented by Chemical Formula 1 or 2 below. The diester-based compound according to the present invention is a material having two ester groups, which has an asymmetric structure in which the numbers of carbons of both alkyl chains with respect to the central atom between the ester groups are different.

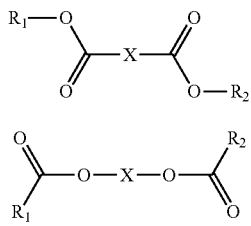

[Chemical Formula 1]

[Chemical Formula 2]

In Chemical Formulas 1 and 2, $R_1$ is a C3~C10 linear alkyl group. Specific examples thereof include propyl, isopropyl, butyl, isobutyl, sec-butyl, tert-butyl, pentyl, isopentyl, neopentyl, tert-pentyl, hexyl, heptyl, octyl, etc.

$R_2$ is different from $R_1$, and $R_2$ is an alkyl group the number of carbons of which is two more than that of $R_1$. For example, in the case where $R_1$ is a C3 propyl group, $R_2$ is a C5 pentyl group the number of carbons of which is two more than that of $R_1$. Here, the number of carbons of $R_2$ falls in the range of C5~C12. Specific examples thereof include pentyl, hexyl, heptyl, octyl, nonyl, decyl, undecyl, and dodecyl.

X is a linear or non-linear C3~C10 alkyl group.

The diester-based base oil according to the present invention has an asymmetric structure in which the numbers of carbons of both alkyl groups $R_1$ and $R_2$ with respect to X between the ester groups are different, namely, a structure in which the number of carbons of $R_2$ is two more than that of $R_1$. The diester-based oil having an asymmetric structure is difficult to crystallize at low temperature, and has high fluidity. The asymmetric diester-based base oil according to the present invention in which the number of carbons of $R_2$ is two more than that of $R_1$ was measured to have lower viscosity and evaporate less at high temperature compared to asymmetric or symmetric diester-based base oil having the same molecular weight. Specifically, the diester-based base oil according to the present invention had a viscosity of 13 cP (centi poise) or less at 20° C. In the case where it was evaporated in a constant-temperature bath at 100° C. for 144 hours, 11 wt % or less of the total weight evaporated.

Thus, the diester-based base oil having low viscosity according to the present invention enables the friction loss of a device to be more effectively reduced. Furthermore, because it evaporates less, stability at high temperature becomes improved. In particular, the lubricating oil composition according to the present invention is adapted for a fluid bearing of a motor for a hard disk, and may be more appropriately used for a hard disk having a size of 2.5 inches or less. In the case of a small hard disk, it should have lower power consumption, and should be stable at high temperature due to rapid rotation of a motor. The lubricating oil composition according to the present invention has low friction loss and is stable at high temperature and thus may satisfy the above requirements of a small hard disk.

Typical examples of the diester-based base oil according to the present invention include 4-(butyryloxy)butyl hexanoate, heptylnonyl adipate, 4-(octanoyloxy)butyl decanoate, octyldecyl adipate, and 4-(nonanoyloxy)butyl undecanoate, as represented by Chemical Formulas 3 to 7 below. Particularly useful is heptylnonyl adipate which is easily prepared and has low viscosity.

[Chemical Formula 3]

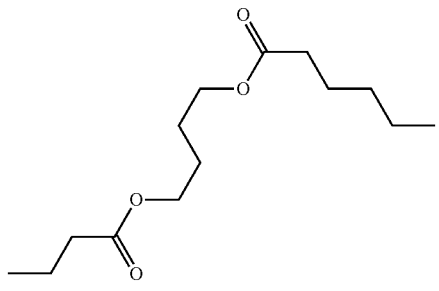

4-(Butyryloxy)butyl hexanoate

[Chemical Formula 4]

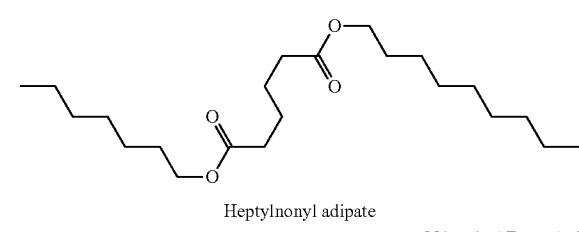

Heptylnonyl adipate

[Chemical Formula 5]

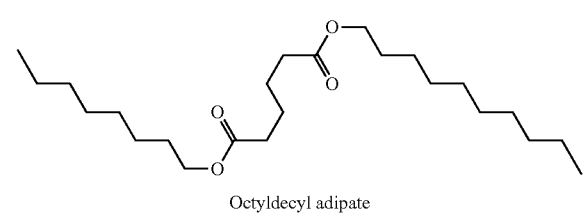

Octyldecyl adipate

[Chemical Formula 6]

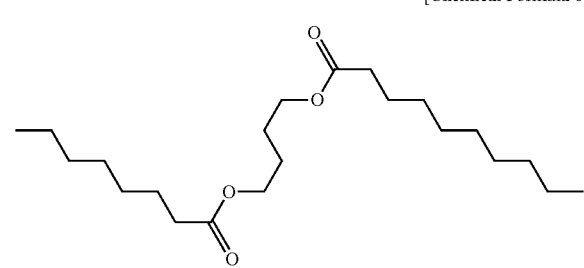

4-(Octanoyloxy)butyl decanoate

[Chemical Formula 7]

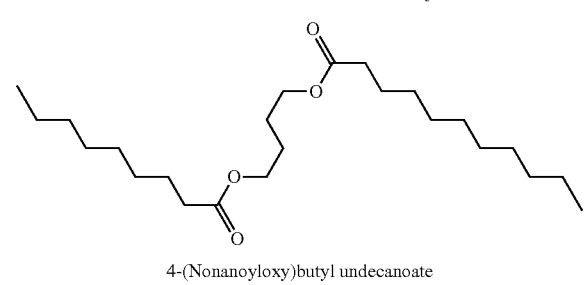

4-(Nonanoyloxy)butyl undecanoate

The lubricating oil composition according to the present invention may further include one or more additives selected from among a cleaning agent, an antioxidant, a viscosity index improver, an anti-wear agent, an anti-corrosive agent, and an antifoaming agent.

The cleaning agent according to the present invention is added so that the lubricating oil composition has oxidation stability. The cleaning agent is an anionic material containing a lipophilic long chain portion and a small amount of anionic or lipophobic portion. Typically, the anionic portion of the cleaning agent is derived from an organic acid, such as sulfuric acid, carboxylic acid, phosphoric acid, phenol or mixtures thereof, and the counter ion is an alkaline earth metal or alkali metal. The cleaning agent may include alkaline earth metal sulfonate, alkaline earth metal phenate, alkaline earth metal salicylate, etc.

As such, the cleaning agent is contained in an amount of 0.01~0.35 wt % in the lubricating oil composition, particularly favored being 0.1~0.3 wt %. If the amount of cleaning agent is less than 0.01 wt %, oxidation stability and lubrication constancy may decrease. In contrast, if the amount thereof exceeds 0.35 wt %, performance of other additives may deteriorate.

The antioxidant is oxidized instead of lubricating oil and thus retards the oxidation of lubricating oil. The antioxidant includes a phenol-based antioxidant and an amine-based antioxidant, and a mixture thereof is also useful. Specific examples of the phenol-based antioxidant include octadecyl-3-(3,5-di-tert-butyl-4-hydroxyphenyl)propionate, 4,4'-methylenebis(2,6-di-t-butylphenol), 4,4'-bis(2,6-di-t-butylphenol), 4,4'-bis(2-methyl-6-t-butylphenol), 2,2'-methylenebis(4-ethyl-6-t-butylphenol), 2,2'-methylenebis(4-methyl-6-t-butylphenol), 4,4'-butylidenebis(3-methyl-6-t-butylphenol), 4,4'-isopropylidenebis(2,6-di-t-butylphenol), 2,2'-methylenebis(4-methyl-6-nonylphenol), 2,2'-isobutylidenebis(4,6-dimethylphenol), 2,2'-methylenebis(4-methyl-6-cyclohexylphenol), etc., and examples of the amine-based antioxidant include monooctyldiphenylamine, monononyldiphenylamine, 4,4'-dibutyldiphenylamine, 4,4'-dipentyldiphenylamine, 4,4'-dihexyldiphenylamine, 4,4'-diheptyldiphenylamine, 4,4'-dioctyldiphenylamine, 4,4'-dinonyldiphenylamine, tetrabutyldiphenylamine, tetrahexyldiphenylamine, tetraoctyldiphenylamine, tetranonyldiphenylamine, etc.

The antioxidant is contained in an amount of 0.01~5 wt % in the lubricating oil composition, particularly favored being 0.01~1.5 wt %. If the amount of antioxidant is less than 0.01 wt %, antioxidative effects may become insignificant. In contrast, if the amount thereof exceeds 5 wt %, it may not dissolve in the lubricating oil composition.

The viscosity index improver alleviates changes in viscosity of the lubricating oil composition depending on changes in temperature, and thus prevents the lubricating oil film from thinning at high temperature. The viscosity index improver is a polymer that expands depending on changes in temperature, and has a small volume at low temperature and thus does not affect the viscosity of the lubricating oil composition, but increases the viscosity of the lubricating oil composition because it is converted into a long chain structure at high temperature.

Examples of the viscosity index improver includes polymethacrylate, dispersed polymethacryalte, olefinic copolymer such as ethylene-propylene copolymer, dispersed olefinic copolymer, styrene-based copolymer such as styrene-diene copolymer, styrene-isoprene copolymer, etc. The viscosity index improver is contained in an amount of 0.5~15 wt % in the lubricating oil composition, particularly favored being 1~10 wt %.

The anti-wear agent is added to suppress the corrosion of the metallic surface. Examples of the anti-wear agent include dibenzyl disulfide, O,O,O-triphenylphosphorothioate, Zn-di-n-butyldithiocarbamate, Mo-dibutyldithiocarbamate, and Zn-methylene-bis-dialkyldithiocarbamate. The anti-wear agent is contained in an amount of 0.01~6 wt % in the lubricating oil composition, particularly favored being 0.01~4 wt %.

The anti-corrosive agent functions to reduce the corrosion of metals that come into contact with the lubricating oil composition. Examples of the anti-corrosive agent include thiadiazole, triazole and succinic acid anhydrides, such as tetrapropenyl succinic acid, tetrapropenyl succinic acid anhydride, dodecenyl succinic acid, dodecenyl succinic acid anhydride, hexadecenyl succinic acid, etc. The anti-corrosive agent is contained in an amount of 0.01~5 wt % in the lubricating oil composition, particularly favored being 0.01~1.5 wt %.

The antifoaming agent functions to suppress the foaming of the lubricating oil composition, and typically includes an organic silicon compound and an organic polymer. Specific examples of the antifoaming agent include silicone oil, fluorosilicone oil, fluoroalkylether. Taking into consideration antifoaming effects and the economic benefits, the antifoaming agent is contained in an amount of 0.005~0.1 wt % in the lubricating oil composition, particularly favored being 0.01~0.1 wt %.

In addition to the above additives, a dispersant, a metal inactivator, a surfactant, an extreme pressure additive, a friction modifier, a coloring agent, or mixtures thereof may be added within the range that does not deteriorate the performance of the lubricating oil composition depending on the end uses.

A better understanding of the present invention may be obtained via the following examples which are set forth to illustrate, but are not to be construed as limiting the present invention.

Example 1

As chemicals having a purity of 95% or more available from Sigma, Aldrich, Merck, TCI, three components including adipic acid, nonyl alcohol, and heptyl alcohol were placed in a 100 ml round-bottom flask, mixed and stirred for about 30 minutes. Subsequently, the reaction was carried out at 150° C. for 24 hours or longer, thus synthesizing heptylnonyl adipate having a molecular weight of 370.6 g/mol.

Example 2

The heptylnonyl adipate synthesized in Example 1 was used as a base oil in an amount of 95 wt % based on the total weight of the composition. Also, 2 wt % of alkaline earth metal sulfonate as a cleaning agent, 1.5 wt % of 2,2'-methylenebis(4-methyl-6-nonylphenol) as a phenol-based antioxidant, and 1.5 wt % of thiadiazole as an anti-corrosive agent were added thereto and stirred at 45~55° C.

Comparative Example 1

As a base oil, dioctyladipate (DOA) available from Aldrich, having the same molecular weight as that of heptylnonyl adipate of Example 1, was used.

Comparative Example 2

Dioctyladipate from Aldrich was used as a base oil in an amount of 95 wt % based on the total weight of the composition. Also, 2 wt % of alkaline earth metal sulfonate as a cleaning agent, 1.5 wt % of 2,2'-methylenebis(4-methyl-6-nonylphenol) as a phenol-based antioxidant, and 1.5 wt % of thiadiazole as an anti-corrosive agent were added thereto and stirred at 45~55° C.

Test Example

The viscosity and the amount of evaporation of the compositions of the examples and comparative examples were measured. The viscosity was measured using a Brookfield DV-III rheometer, and in order to check the effects depending on the temperature, respective components were measured in the three temperature ranges (20° C., 0° C., −10° C.). The amount of evaporation was measured by placing 5 g of each of the lubricating oil compositions on an evaporating dish made of SUS, and placing the dish into a constant-temperature bath at 100° C. The test was performed for 144 hours (6 days), and the initial weight of the evaporating dish containing the composition and the weight after evaporation at 100° C. for 144 hours were measured and the amount of evaporation was compared.

TABLE 1

|  | Molecular Weight | Viscosity (cP) | | | Amount of Evaporation (wt %) |
| --- | --- | --- | --- | --- | --- |
|  | (g/mol) | 20° C. | 0° C. | −10° C. | (100° C./144 hr) |
| Ex. 1 | 370.6 | 12.6 | 30.5 | 51.9 | 7.56 |
| Ex. 2 | 370.6 | 15.6 | 35.1 | 59.7 | 4.99 |
| C. Ex. 1 | 370.6 | 13.3 | 34 | 60.2 | 15.3 |
| C. Ex. 2 | 370.6 | 17.4 | 41.6 | 71.3 | 7.12 |

As is apparent from Table 1, the lubricating oil composition (Example 2) according to the present invention had lower viscosity and evaporated less at high temperature compared to the comparative lubricating oil composition having the same molecular weight (Comparative Example 2).

As described hereinbefore, the present invention provides a lubricating oil composition having low viscosity and a small amount of evaporation at high temperature, using, as a base oil thereof, a diester-based base oil having an asymmetric structure with respect to a central atom.

Although the embodiments of the present invention regarding the lubricating oil composition have been disclosed for illustrative purposes, those skilled in the art will appreciate that a variety of different modifications, additions and substitutions are possible, without departing from the scope and spirit of the invention as disclosed in the accompanying claims. Accordingly, such modifications, additions and substitutions should also be understood as falling within the scope of the present invention.

What is claimed is:

1. A lubricating oil composition, comprising a diester-based base oil of heptylnonyl adipate represented by Chemical Formula 4 below:

[Chemical Formula 4]

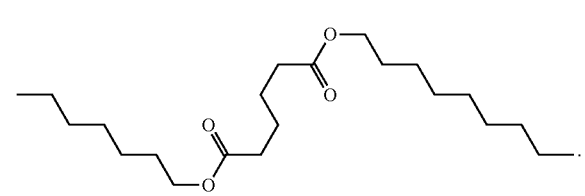 [SMILES: CCCCCCCCCOC(=O)CCCCC(=O)OCCCCCCC]

2. The lubricating oil composition of claim 1, further comprising one or more additives selected from the group consisting of a cleaning agent, an antioxidant, a viscosity index improver, an anti-wear agent, an anti-corrosive agent, and an antifoaming agent.

3. The lubricating oil composition of claim 1, which has a viscosity of 13 cP (centi poise) or less at 20° C.

4. The lubricating oil composition of claim 1, which is used for a fluid bearing of a motor for a hard disk.

* * * * *